United States Patent [19]
Nieder

[11] Patent Number: 5,411,555
[45] Date of Patent: May 2, 1995

[54] KNEE JOINT PROSTHESIS KIT

[75] Inventor: Elmar Nieder, York, Germany

[73] Assignee: GMT Gesellschaft Fur Medizinische Technik GmbH, Hamburg, Germany

[21] Appl. No.: 897,468

[22] Filed: Jun. 11, 1992

[30] Foreign Application Priority Data

Jun. 11, 1991 [DE] Germany .............................. 41 19 226

[51] Int. Cl.6 .................................................... A61F 2/38
[52] U.S. Cl. .......................................... 623/20; 623/18
[58] Field of Search ......................... 623/18, 19, 20, 23

[56] References Cited

U.S. PATENT DOCUMENTS

| | | | |
|---|---|---|---|
| 4,219,893 | 9/1980 | Noiles | 623/20 |
| 4,358,859 | 11/1982 | Schurman et al. | 623/20 |
| 4,538,305 | 9/1985 | Engelbrecht et al. | 623/20 |
| 4,790,853 | 12/1988 | Engelbrecht et al. | 623/20 |
| 4,834,758 | 5/1989 | Lane et al. | 623/20 |
| 5,139,521 | 8/1992 | Schelhas | 623/20 |

FOREIGN PATENT DOCUMENTS

| | | | |
|---|---|---|---|
| 2601873 | 1/1988 | France | 623/20 |
| 2744710 | 4/1979 | Germany | 623/20 |

Primary Examiner—David Isabella
Attorney, Agent, or Firm—Darby & Darby

[57] ABSTRACT

A knee joint prosthesis kit which is composed of a femoral component having a housing and a shank implantable in a femur, a first tibial component having a first hinge leaf and a shank implantable in a tibia, a second tibial component having a second hinge leaf and a shank implantable in a tibia, and a pintle which can pivotally connect the housing of the femoral component with that tibial component whose leaf is inserted into the housing. This enables the femoral component and the first tibial component to pivot relative to each other about a first axis which is normal or nearly normal to the shanks of the coupled components so that the resulting prosthesis can serve as a flexion type prosthesis. The second tibial component has a platform which carries the second leaf in such a way that the latter can turn relative to the platform and relative to the shank of the second tibial component about a second axis which is normal to the first axis when the second leaf is received in the housing and is secured thereto by the pintle. This enables the femoral component and the second tibial component to be used as a combined flexion and rotation type knee joint prosthesis.

59 Claims, 4 Drawing Sheets

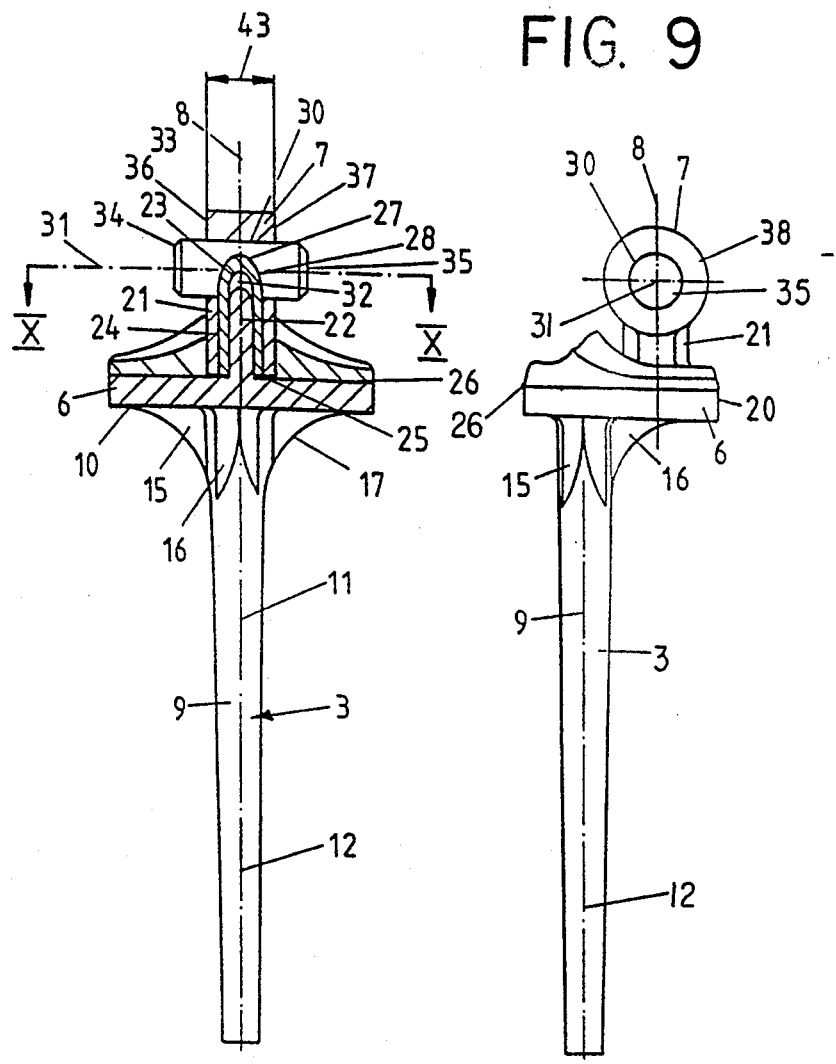

KNEE JOINT PROSTHESIS KIT

BACKGROUND OF THE INVENTION

The invention relates to improvements in knee joint prostheses. More particularly, the invention relates to improvements in devices which are used in such prostheses to establish an articulate connection between the femoral and tibial components. Still more particularly, the invention relates to improvements in knee joint endoprostheses of the type described, claimed and shown in commonly owned copending patent application Ser. No. 07/800,327 filed Nov. 29, 1991 by Eckart Engelbrecht and Elmar Nieder for "Knee joint prosthesis".

Knee joint prostheses can be divided into two main categories, namely partial and full prostheses. Each of these prostheses is intended to enable a patient to walk again or to enhance the ability of a patient to walk, and each of these prostheses can be utilized to at least partially restore the integrity of a knee joint which is damaged as a consequence of a disease and/or as a result of trauma.

A partial prosthesis restores the surfaces of femoral and/or tibial condyles and cooperates with the ligaments (including the medial, lateral and crucial ligaments). A properly implanted partial prosthesis cooperates with the ligaments in the transmission of loads (mechanical functions) as well as in regulation of various movements. A prerequisite for proper functioning of a partial prosthesis is that the ligaments be at least substantially intact, i.e., such prostheses should not be called upon to compensate for certain diseases or defects of the knee joint which involve damage to the ligaments. The four most common types of such diseases or defects are genu varum, genu valgum, genu flexum and genu laxum. Decompensation would entail shrinkage or overextension of passive and active stabilizers in a knee joint or a combination of both. Ligaments constitute the passive stabilizers of a knee joint, and the active stabilizers include the tendons of muscles which extend across the knee joint. Stabilizers can be classified as medial, lateral or dorsal stabilizers (provided that the stretching system is disregarded). The functioning of a partial prosthesis is unsatisfactory, and its useful life is too short, if the active and/or passive stabilizers are damaged in a manner as outlined above, i.e., if such stabilizers have undergone shrinkage and/or overextension. The reason is that a partial prosthesis constitutes a totally uncoupled system. A partial prosthesis which employs a plane plateau (also called sled type prosthesis) can be implanted only when the stabilizers are entirely intact. A partial prosthesis which utilizes a slightly grooved or otherwise uneven plateau can compensate, to a certain extent, for minor weakening of active and/or passive stabilizers.

A total prosthesis must be implanted in the event of destabilization of passive and/or active stabilizers. Such prostheses take over not only the mechanical functions (i.e., transmission of loads) but also the regulation of movements of the femur and tibia relative to each other. A total prosthesis does not afford to the knee a freedom of movement matching that which is afforded by a partial prosthesis. On the other hand, a properly implanted total prosthesis imparts to the knee joint a higher degree of stability than a partial prosthesis even though the passive and/or active stabilizers of the repaired knee joint are defective.

Total prostheses include so-called hinge- or flexion-type prostheses wherein the femoral and tibial components can perform a single movement relative to each other, namely pivoting about a predetermined axis which is defined by the shaft or pintle of the hinge serving to articulately connect the two components. The single form of movement which is permitted by such types of prostheses is known as monocentric flexing. Another class of total prostheses embraces the so-called rotational prostheses which enable the tibial and femoral components to perform any movements afforded by a flexion-type prosthesis plus rotation of the tibia relative to the femur. Tibial rotation serves to protect the connections between the shanks of the two components and the bones into which the shanks are implanted as well as the bones themselves because the moments which develop as a result of rotation about the longitudinal axis of the respective leg are transmitted to the remaining intact soft parts in the region of the knee joint. For the above reasons, the useful life of connections between the implanted shanks of femoral and tibial components of a rotational prosthesis and the respective bones is longer than that of connections in a flexion-type total prosthesis. Moreover, the likelihood of fracturing the tibia and/or the femur in the event of trauma is less pronounced than if the implanted prosthesis is a flexion-type prosthesis. It is a well known fact that the useful life of connections between the shanks and the bones into which the shanks are implanted is longer if the total prosthesis enables the femur and the tibia to perform flexural as well as rotational movements relative to each other. Therefore, a rotational prosthesis is normally preferred over a purely flexural prosthesis. On the other hand, limitations upon the usability of a rotational prosthesis are imposed by the nature of deformity of the affected knee joint.

Genu flexum (which could be termed an overly bent knee) is a deformity which prevents the afflicted knee joint from permitting the tibia to move to a fully extended position of substantial alignment with the femur. The reason for the development of such deformity is stretching of the rear (dorsal) capsula and/or shrinkage of tendons which are active during flexing of the tibia. In order to remedy the situation, a surgeon will detach the rear capsula at the point of connection to the dorsal side of the thigh. In most cases of a contraction of a tendon, such operative treatment suffices to ensure that, once the rotational prosthesis is implanted, the knee joint regains its ability to permit full extension or stretching of the shin relative to the thigh. If the genu flexure is very pronounced, i.e., if mere detachment of the rear capsula does not suffice to remedy the situation, this indicates a pronounced shrinkage of the tendons which are necessary to flex the shin relative to the thigh. The possibilities to remedy such defects are twofold, namely: One can resort to so-called lengthening (Z-plastic) of affected tendons or to stepwise resection of the tibia. The lengthening of tendons is a time-consuming operation which necessitates additional surgery and lengthy postoperative immobilization of the knee which is contrary to the presently preferred procedure of mobilizing a patient as soon as possible following implantation of a knee prosthesis. Therefore, specialists in the field of implantation of knee joint endoprostheses prefer to resort to stepwise recession until the thus corrected knee joint permits full stretchability of the shin.

If such full stretchability is achieved only upon extensive tibial resection, this results in mere pseudostability in extended position of the shin, and such pseudostability is attributable to stretching of the remaining shortened dorsal stretching tendons. If a patient who has undergone such treatment decides to bend her or his shin, all of the structures which extend across the knee, the stretching system and the remaining capsular band sleeve or its scarred regenerate are too long. This brings abut the danger of subluxation or total dislocation in the joint between the shaft and the sleeve of the rotational prosthesis, both likely to affect the functioning and/or the tissue in the region of the knee. Therefore, when the required treatment involves stepwise resection of the tibia, the surgeon in charge will normally decide to implant a flexion-type prosthesis which merely permits flexing of the shin and thigh relative to each other about a single axis.

Genu varum (known as bowleg) is attributable primarily or exclusively to loss of the level of medial femoral and tibial condyles. Decompensation of passive and active medial and lateral stabilizers is infrequent and develops at a more advanced age, i.e., shrinkage of medial structures and overextension of lateral structures are infrequent and develop only when the bowleg becomes very pronounced. Therefore, the possibilities of implanting a rotational prosthesis in the knee of a bowlegged patient are practically unlimited because the ligaments which have undergone contraction or excessive stretching are detached in the course of the normal operative procedure and the scarred regenerate of lateral ligaments and capsula normally suffices to establish and guarantee intimate contact between the femoral and tibial components. The need for implantation of a flexion-type knee joint endoprosthesis in the case of a bowleg arises only when the genu varum develops simultaneously with highly pronounced genu flexum, namely when the aforedescribed extensive resection of the tibia is necessary to correct the flexural component.

Genu valgum (known as knock-knee) is attributable to premature decompensation of stabilizers. Such defects can be remedied, practically at any stage, by implantation of a rotational prosthesis. Decompensation of stabilizers in a genu valgum does not, by itself, limit the usefulness of a rotational prosthesis because the lateral ligaments at the femoral condylum must be detached anyway and the scarry regenerated lateral ligament sleeve guarantees the establishment of an intimate contact between the components. However, genu valgum can involve complicating additional problems. The active stabilizers (musculus bicepts and its tendon, tractus iliotibialis, musculus peblitius and its tendon and the lateral gastocnemius head) predominate at the exterior of the knee joint, and such active stabilizers turn outwardly in inclined position of the tibia. This is their normal additional function. However, if such active stabilizers and/or their tendons happen to shrink as a result of premature decompensation in the case of genu valgum, this is further complicated by improper positioning of the shin upon completion of turning in an outward direction. This can be remedied by resorting to the aforediscussed (Z-plastic) treatment (lengthening)of the active stabilizers and their tendons. Such treatment is expensive, as in the case of flexural tendons, and necessitates postoperative immobilization of the knee. Therefore, specialists in the relevant field of surgery prefer to remedy a genu valgum with the aforedescribed side effect (improper positioning of the shin upon turning in outward direction) by notching or even removing the active outwardly turning shrunk stabilizers and by implanting a flexion type prosthesis in order to thus compensate (a) for weakening of the knee due to removal of stabilizers and (b) for the eventually remaining tendency of the shin to assume an improper position upon turning in an outward direction.

Genu laxum is a deficiency which is attributable to extreme overextension of all stabilizers. Therefore, such problem cannot be overcome by implanting a total prosthesis of the type known as rotational prosthesis, i.e., the only remedy at the disposal of a surgeon is to implant a hinge- or flexion-type prosthesis in order to keep the tibial and femoral components together.

The aforediscussed limitations regarding the utilization of various types of knee prostheses apply essentially for the most frequently occurring problems, namely the idiopathic (innate) arthrosis. In the case of rheumatic arthritis, which is the next most frequently occurring class of illnesses, and which can also necessitate the implantation of a knee joint prosthesis, the aforediscussed considerations regarding the utility or desirability of various types of knee joint prostheses are even more pronounced because the muscles of a patient who is suffering from rheumatism are weakened anyway. In many instances, rheumatic arthritis entails the development of genu valgum with the aforediscussed additional complication (improper positioning of the shin upon turning in an outward direction). Therefore, the implantation of a simple flexion-type knee joint prosthesis is preferred under such circumstances or most by many surgeons.

Knowledge of various afflictions of knee joints has been greatly expanded during the last years. Furthermore, specialists in this area have determined, even more reliably, that extensive examinations with assistance from X-ray equipment and/or other recently developed sophisticated apparatus still cannot guarantee optimal advance selection of the most satisfactory prostheses to be implanted into the knees of patients suffering from the aforediscussed afflictions. In other words, it is not possible to predictably plan an operation which involves the implantation of a partial or total knee joint prosthesis prior to actual start of surgery. Thus, the surgeon must inspect an afflicted knee in the course of an operation in order to select a proper prosthesis which is best suited for implantation into the body of a patient on the operating table. For example, if the illness to be remedied is genu flexum, the surgeon must first detach the rear capsula prior to reaching a decision regarding the amount of bone tissue to be removed from the tibia. This, in turn, will enable the surgeon to decide which of the total prostheses is called for under the existing circumstances. In other words, a hospital or a clinic specializing in operations of knee joints must maintain a variety of prostheses in order to make sure that a proper prosthesis will be available if the ultimate decision regarding the type of prosthesis to be implanted departs from the tentative decisions which were reached upon completion of preliminary examination of the afflicted knee joint.

OBJECTS OF THE INVENTION

An object of the invention is to provide a knee joint endoprosthesis which is more versatile than heretofore known prostheses.

Another object of the invention is to provide a total knee joint prosthesis which is more versatile than heretofore known total knee joint prostheses.

A further object of the invention is to provide a novel and improved flexion-type prosthesis.

An additional object of the invention is to provide a novel and improved rotational prosthesis.

Still another object of the invention is to provide a total knee joint prosthesis certain parts of which can be used as elements of a flexion-type prosthesis or as elements of a rotational prosthesis.

A further object of the invention is to provide a prosthesis which renders it possible to reduce the supply of prostheses which must be maintained in stock in a hospital or other establishments specializing in the implantation of knee joint prostheses.

Still another object of the invention is to provide a knee joint prosthesis which enables a surgeon to implant a portion of such prosthesis prior to deciding upon the exact nature of the remaining portion or portions of the prosthesis.

Another object of the invention is to provide a novel and improved connection between the shanks of the femoral and tibial components of a knee joint prosthesis.

An additional object of the invention is to provide a novel and improved knee joint prosthesis kit.

A further object of the invention is to provide a novel and improved total knee joint prosthesis kit.

Another object of the invention is to provide a knee joint prosthesis which is constructed and assembled in such a way that the surgeon in charge can make last-minute decisions regarding the exact nature of the prosthesis to be implanted while the operation upon the knee of a patient is already in progress.

Still another object of the invention is to provide a novel and improved method of enhancing the versatility of a total knee joint prosthesis.

SUMMARY OF THE INVENTION

The invention is embodied in a knee joint prosthesis kit which comprises first and second tibial components each including an elongated shank implantable in a tibia, a femoral component having a shank implantable in a femur, means for movably connecting the first tibial component with the femoral component so that the first tibial component is pivotable relative to the femoral component about a first axis, and means for movably securing the second tibial component to the femoral component in lieu of the first tibial component so that the second tibial component is pivotable relative to the femoral component about the first axis as well as about a second axis which is at least substantially normal to the first axis.

The connecting means preferably comprises a first hinge having a first leaf provided on the first tibial component, a second leaf provided on the femoral component, and a pintle serving to articulately connect the leaves to each other and to define the first axis while the two leaves are articulately connected to each other.

The second tibial component comprises a support at one end of the respective shank, and the securing means preferably comprises a second hinge having a third leaf, means for movably mounting the third leaf on the support for rotation about the second axis, and the aforementioned pintle. The pintle serves to articulately connect the second and third leaves to each other and to define the first axis while the second and third leaves are articulately, connected to each other.

The first tibial component preferably further comprises a support which is disposed at one end of the respective shank and carries the first leaf. The supports have sides (undersides) which face away from the leaves of the respective tibial components, and the shanks of the tibial components are or can be substantially normal to such sides of the respective supports. The shank of each tibial component is preferably pivotable in a plane which is normal to the first axis when the leaf of either of the two tibial components is articulately connected to the second leaf.

Each support has a patellar (anterior or front) and a dorsal (rear) end. The shanks of the tibial components extend from the undersides of the respective supports (particularly at right angles to such undersides), and at least one of the two tibial components is provided with a plurality of reinforcing portions (e.g., in the form of ribs) which are disposed at the underside of the respective support and extend between the support and the adjacent (upper) end of the respective shank. Such reinforcing portions can include a rib which is disposed at the rear end of the respective support in a first plane which is normal to the first axis when the leaf of the at least one tibial component is articulately connected to the second leaf. Two additional reinforcing ribs can be disposed in a second plane which is substantially normal to the first plane.

The femoral component is preferably provided with a housing disposed at one end of the respective shank and including two preferably parallel walls which constitute or include the second leaf. The housing receives at least a portion of the first leaf when the femoral component is connected with the first tibial component, or the third leaf when the femoral component is assembled with the second tibial component.

The walls of the housing can be provided with skids which are adjacent and can (directly or indirectly) engage the support of the first or second tibial component. Such walls are disposed at opposite sides of a plane which is normal to the first axis when the second leaf is articulately connected to one of the first and third leaves. A track of each support has two portions, one for each of the two skids, and the two portions of each track are disposed at the respective lateral portions of the corresponding support and at opposite sides of the aforementioned plane. The arrangement is preferably such that each lateral portion of a support carries one portion of the respective track. The lateral portions of each support can be provided with top faces which slope upwardly toward a cam at the front end of the respective support.

The femoral component and the first or second tibial component (whichever is coupled to the femoral component) are pivotable relative to each other about the first axis between extended (first) positions (in which the shank of the femoral component is or can be substantially aligned with or parallel to the shank of the respective tibial component) and mutually inclined (second) positions in which the shanks of the femoral component and the respective tibial component make an oblique angle. The housing of the femoral component can be provided with a concave follower which abuts the respective cam when the femoral component and the tibial component which is coupled thereto assume the aforementioned extended or first positions relative to each other.

The upper ends of the shanks forming part of the tibial components are preferably spaced apart from the front ends of the respective supports. The aforementioned reinforcing portions or ribs are preferably positioned in such a way that two ribs of each support are located in a plane which is substantially parallel to the first axis when the leaf of the respective tibial component is articulately connected to the second leaf. The plane of the two ribs is nearer to the front end than to the rear end of the respective support. A third reinforcing portion or rib of each tibial component is preferably located in a plane which is normal to the plane of the two ribs, and such third reinforcing portion or rib preferably extends at least close to the rear end of the respective support.

The first axis is preferably closer to the rear end than to the front end of the support forming part of the tibial component which is coupled to the femoral component.

The first axis is preferably spaced apart from the support of the tibial component which is coupled to the femoral component a distance of between approximately 25 and 30 min.

The diameter of the pintle can equal or approximate 20 mm.

The aforementioned skids forming part of the housing of the femoral component have at least partly convex surfaces which confront the support of that tibial component whose leaf is articulately connected to the second leaf (i.e., to the housing of the femoral component). Such convex surfaces are spaced apart from the first axis a distance which is preferably in the range of 20–25 ram. Each such convex surface can extend along an arc of approximately 180°, i.e., approximately halfway around the first axis when the second leaf is articulately connected to one of the first and third leaves.

The housing of the femoral component is provided with a front surface which is disposed at the front end of the housing and extends to the respective shank. The front portions of the convex surfaces of the skids preferably extend to the lowermost portion of the front surface of the housing. The radii of curvature of the front portions of such convex surfaces are preferably larger than the radii of curvature of their rear portions (at the rear end of the housing). The front surface of the housing of the femoral component is preferably offset in a direction from the front end toward the rear end of that support which forms part of the tibial component whose leaf is articulately connected with the housing, i.e., with the second leaf, when the femoral component and the tibial component which is then articulately connected to the femoral component assume the aforementioned first or extended positions relative to each other.

The housing of the femoral component preferably further comprises a concave follower which confronts the support of that tibial component whose leaf is articulately connected to the housing, and each support then includes a cam which is adjacent and guides the follower in the first positions of the respective components or during movement of the respective components between first and second (mutually inclined) positions.

The rear end of the housing preferably extends rearwardly beyond the rear end of the support carrying that leaf which is articulately connected to the second leaf while the femoral component and the tibial component which is coupled thereto assume the extended positions relative to each other. The front surface at the front end of the housing makes an acute angle with the adjacent (upper) side of the support carrying that leaf (namely the first or the third leaf) which is articulately connected to the housing, again while the femoral component and the tibial component which is coupled thereto assume the first or extended positions relative to each other.

That (lowermost) portion of the front surface of the housing which is adjacent the skids of the two walls of such housing is preferably aligned with the front portion of the shank depending from the support whose leaf is articulately connected to the housing while the femoral component and the tibial component which is coupled thereto assume the first positions relative to each other.

The housing of the femoral component further comprises a top wall which is or can be at least substantially normal to the front surface of the housing and carries the shank of the femoral component. The lower end of the shank of the femoral component (i.e., that end which is rigid with the top wall) is or can be adjacent or immediately adjacent the front surface of the housing.

When the femoral component is coupled to one of the tibial components and such components are moved to the extended positions relative to each other, the axis of the shank of the femoral component is or can be at least substantially parallel to the axis of the shank of the tibial component. The axis of the shank of the tibial component is then nearer to the first axis than the axis of the shank of the femoral component. The planes which include the axes of such shanks (and which are parallel or nearly parallel to each other in the extended positions of the respective components) can be spaced apart from each other a distance of 0.5 to 4 min.

The axis of the shank of the femoral component makes a relatively small acute angle (the so-called valgus angle) with a plane which is normal to the first axis. Such acute angle can be between approximately 3 and 8°.

At least one of the shanks preferably tapers in a direction away from the respective leaf. For example, at least one of the shanks can resemble an elongated slender cone. The external surface of at least one of the shanks is preferably smooth, and at least one shank can have a substantially circular cross-sectional outline. Furthermore, at least one of the shanks can have a facetted external surface with one or more facets or flats extending longitudinally of such shank.

The aforementioned parallel walls of the housing of the femoral component have external surfaces which are or can be at least substantially normal to the front surface of the housing. The external surfaces are or can be plane surfaces, and the walls which constitute the second leaf have aligned bores or holes for end portions of the pintle. The median portion of the pintle extends through a bore or hole in the first or third leaf, depending upon whether the housing is articulately connected to the leaf of the first or second tibial component.

That end of at least one of the shanks which is remote from the respective leaf can be provided with suitable centering means, e.g., a prong or cap having a substantially stellate cross-sectional outline.

The distance between the external surfaces of those walls of the housing of the femoral component which constitute the second leaf can be in the range of 30 to 35 mm, e.g., at least close to 30 mm. Furthermore, each such wall can have a thickness of between 5 and 8 mm, preferably at least close to 5 mm.

The walls which constitute the second leaf can be provided with extensions having (upper) sides which are engaged by portions of a femur into which the shank of the femoral component is implanted. The external surfaces of these walls are adjacent the aforementioned sides of the corresponding extensions. The skids can be provided on the extensions and their surfaces which confront one of the supports when the femoral component is coupled with one of the tibial components are preferably located opposite the aforementioned (femur-engaging) sides of the extensions. The length of the sides of the extensions and of the surfaces of the respective skids is preferably the same (such length is measured in a direction from the front side toward the rear side of the housing of the femoral component). The (upper) side of each extension preferably merges gradually into the external surface of the corresponding wall of the housing. Each skid can have a thickness of 1 to 3 min.

The rear end of each support can be provided with a recess and with two convex portions which flank the recess. The convex portions are adjacent the surfaces of the skids when the respective support (and more particularly the leaf which is carried by such support) is articulately connected to the housing. The convex portions of each support have parts which are adjacent the front end of the support, and each support further comprises a cam having a surface extending between the surfaces of the respective convex portions.

The first leaf has an edge face which is or can be adjacent the rear end of the respective support and is also adjacent the aforementioned recess of such support. The upper side of each support is preferably spaced apart from the first axis a distance of 25 to 30 mm when the respective tibial component is coupled to the femoral component.

The surfaces of the skids are elongated and preferably include convex portions which extend longitudinally of the housing in a direction from the front surface toward the rear end of the housing.

The means for movably mounting the third leaf on the support of the second tibial component can include a shaft which is provided on the support of the second tibial component, and a bearing (e.g., a cupped friction bearing of suitable plastic material) which surrounds the shaft and is received in a bore of the third leaf. Such bearing is preferably spaced apart from the support of the second tibial component and preferably includes a portion which extends into a socket of the pintle when the third leaf is articulately connected to the housing (i.e., to the second leaf).

The novel features which are considered as characteristic of the invention are set forth in particular in the appended claims. The improved kit itself, however, both as to its construction and the mode of utilizing the same, together with additional features and advantages thereof, will be best understood upon perusal of the following detailed description of certain presently preferred specific embodiments with reference to the accompanying drawing.

BRIEF DESCRIPTION OF THE DRAWING

FIG. 8 is a partly elevational and partly vertical sectional view of the second tibial component;

FIG. 9 is a view as seen from the left-hand side of FIG. 8;

FIG. 10 is an enlarged horizontal sectional view substantially as seen in the direction of arrows from the line X—X in FIG. 8;

DESCRIPTION OF PREFERRED EMBODIMENTS

Figure 1:
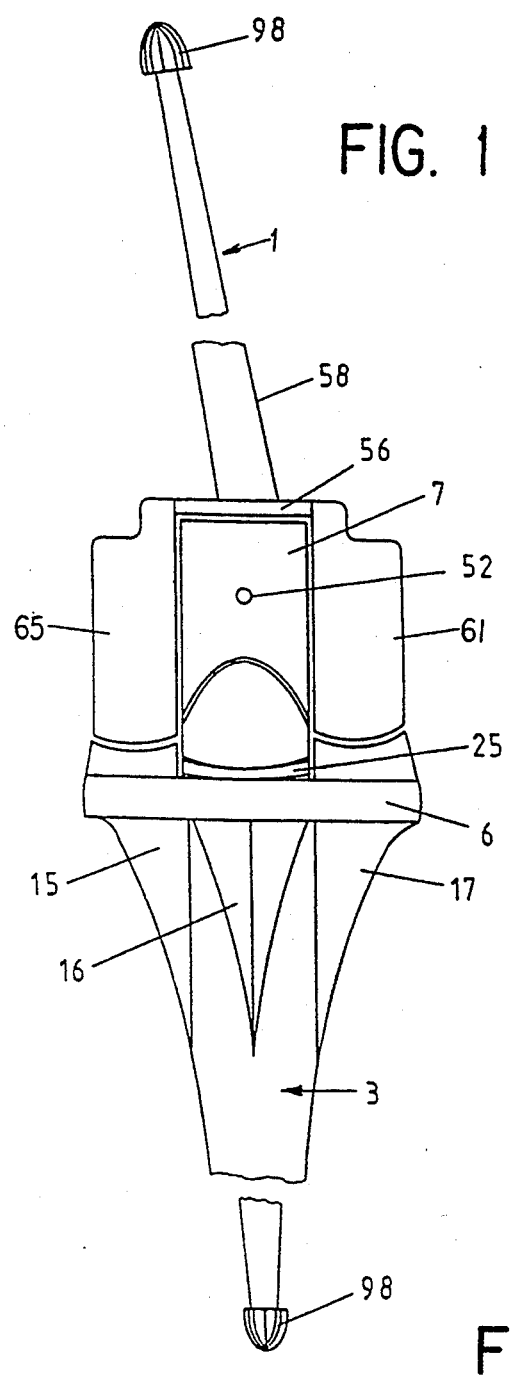
FIG. 1 is a fragmentary rear elevational view of a knee joint prosthesis which comprises a femoral component and a first tibial component.
Figure 2:
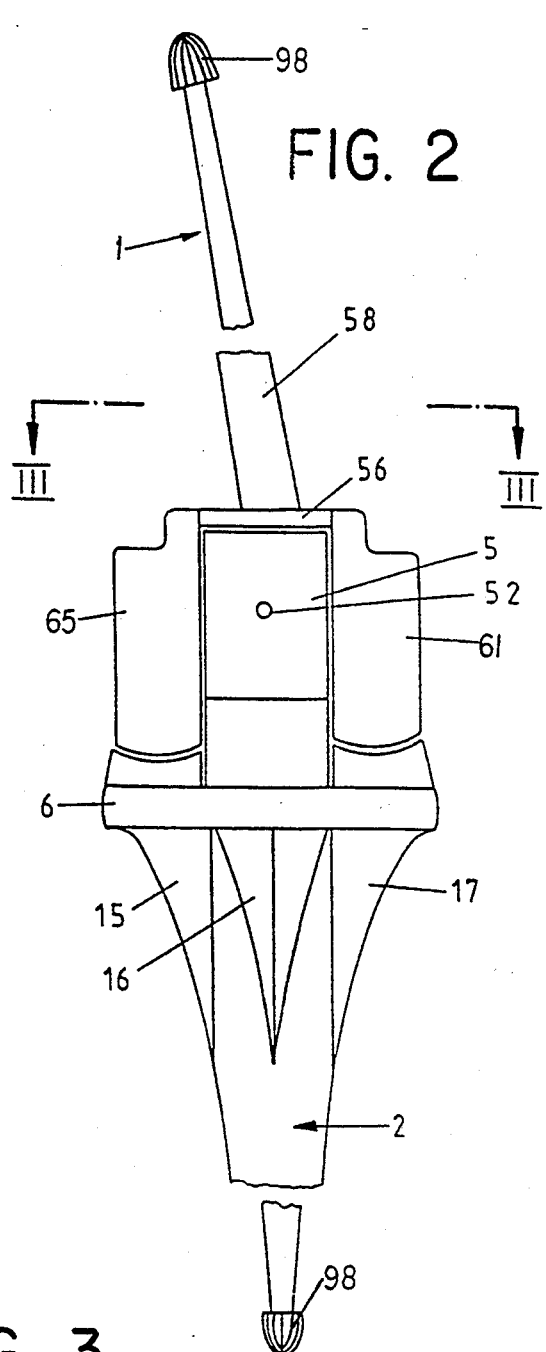
FIG. 2 is a similar fragmentary rear elevational view of a knee joint prosthesis which comprises the femoral component of FIG. 1 and a second tibial component.

The drawing shows the constituents of a knee joint endoprosthesis kit which is composed of a femoral component 1, a first tibial component 2, a second tibial component 3, a first hinge 4 (including a pintle 35) constituting or forming part of means for movably connecting the first tibial component 2 with the femoral component 1 so that the components 1 and 2 are pivotable relative to each other about a first axis 31, and a second hinge 7 (including the pintle 35 and a shaft 22) constituting or forming part of means for movably securing the second tibial component 3 to the femoral component 1 so that the components 1 and 3 can be pivoted relative to each other about the first axis 31 as well as abut a second axis 8 which is at least substantially normal to the first axis 31. The femoral component 1 comprises an elongated shank 58 which is implantable in a femur (not shown) in a manner not forming part of the present invention, the first tibial component 2 comprises an elongated shank 9 which can be implanted in a tibia (not shown) in a manner not forming part of the present invention, and the second tibial component 3 also comprises an elongated shank 9 which can be implanted in a tibia when the surgeon in charge of implanting a knee joint prosthesis decides that a patient is best served by a rotational prosthesis (including the components 1 and 3) rather than by a flexion-type prosthesis (including the components 1 and 2).

Each of the two tibial components 2 and 3 comprises a support or plateau 6 which is integral with or is rigidly secured to the adjacent upper end of the respective shank 9 in such a way that the shank 9 is normal or substantially normal to the adjacent underside or bottom surface 10 of the respective support 6. When the tibial component 2 or 3 is properly coupled to the femoral component 1, the respective shank 9 can pivot relative to the shank 58 of the component 1 in a plane 11

Figure 11:
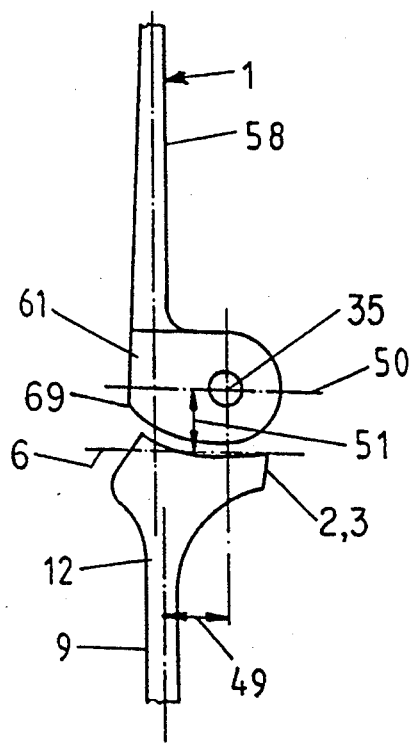
FIG. 11 is a schematic smaller-scale elevational view of an assembled knee joint prosthesis showing the femoral component and one of the tibial components in extended positions relative to each other.

(extending at right angles to the plane of FIG. 6 or 8 and in the plane of FIG. 11 or 12) which is normal to the first axis 31. The components 1 and 2 or 1 and 3 can pivot relative to each other between (a) extended or first positions which are shown in FIG. 11 (and in which the shanks 58 and 9 are at least nearly aligned) and (b) mutually inclined second positions (shown in FIG. 12) in which the shanks 58 and 9 make an oblique angle 13. The longitudinal axes of the shanks 9 are shown at 12.

The shanks 9 of the tibial components 2 and 3 are nearer to the front or patellar ends 14 than to the rear or dorsal ends 20 of the respective supports 6. Each tibial component further comprises reinforcing portions which are located at the bottom surface or underside 10 of the respective support 6 and extend between such support and the adjacent (upper) end of the respective shank 9. FIGS. 1, 2 and 6 to 9 show three reinforcing portions 15, 16 and 17 in the form of ribs which taper from the respective underside 10 downwardly toward the respective shank 9. The reinforcing portions or ribs 15 and 17 are located in a plane which is normal to the plane 11 and are disposed at opposite sides of the upper end of the respective shank 9. The rib 16 is located in or at the plane 11, and its uppermost part preferably extends from the upper end of the respective shank 9 at least close to or all the way to the rear end 29 of the respective support 6. The uppermost parts of the reinforcing ribs 15 and 17 terminate at or at least close to the respective lateral portions 18, 19 of the corresponding support 6.

The first hinge 4 comprises the pintle 35, a first leaf 5 (see particularly FIGS. 6 and 7) which is provided at the upper side or surface 26 of the support 6 of the tibial component 2 at the rear end 20 of such support, and a second leaf including two spaced-apart parallel walls 61 and 65 (see particularly FIGS. 4 and 5) forming part of a block-shaped housing or casing which is integral with the adjacent end of the shank 58. The leaf 5 is received in a chamber 46 of the housing of the femoral component 1 between the walls 61, 65 of the second leaf when the components 1 and 2 are properly coupled to each other so that their shanks 58 and 9 can pivot between the extended positions of FIG. 11 and the mutually inclined positions of FIG. 12. FIG. 6 shows that the lower portion of the leaf 5 is integral (of one piece) with the respective support 6.

The second hinge 7 comprises the pintle 35, the second leaf including the walls 61, 65 of the housing of the femoral component 1, and a third leaf 21 (see particularly FIGS. 8 and 9) which is rotatably mounted on the shaft 22 of the respective support 6 (of the tibial component 3) and is receivable in the housing of the femoral component 1 in lieu of the first leaf 5. Thus, one and the same femoral component 1 can be properly coupled to the tibial component 2 or to the tibial component 3 in order to assemble a flexion-type prosthesis (including the components 1 and 2) or a rotational prosthesis (including the components 1 and 3). The axis 8 of the shaft 22 is normal to and intersects the axis 31 of the pintle 35 when the second hinge 7 is fully assembled.

A cupped friction bearing 23 of the hinge 7 is interposed between the leaf 21 and the shaft 22. This friction bearing is made of a suitable plastic material and its cylindrical lower portion is snugly received in a bore or hole 24 of the leaf 21. The inner diameter of the bearing 23 matches the diameter of the shaft 22. This ensures that the leaf 21 can turn relative to the support 6 and shaft 22 of the second tibial component 3 about the axis 8 which coincides with the axis of the shaft 22 and intersects the axis 31 of the properly installed pintle 35 at an angle of 90°. The lower end 25 of the plastic bearing 23 is slightly spaced apart from the adjacent portion of the upper side or surface 26 of the support 6 forming part of the second tibial component 3. This ensures that the bearing 23 does not bear and rub against the support 6 of the component 3 when the second hinge 7 is fully assembled, i.e., when the assembled prosthesis is a rotational prosthesis.

The cupped upper end portion 27 of the friction bearing 23 is snugly receivable in a complementary socket or recess 28 of the pintle 35. The latter is received in and its end portions 34 extend beyond both sides 36, 37 of the third leaf 21. The axis 32 of the bearing 23 coincides with the second axis 8, and the dome-shaped external surface 33 of the upper end portion 27 abuts the adjacent surface bounding the socket 28 to ensure that the axis 31 is maintained at a desired optimal distance 51 (e.g., 25 to 30 ram) from the upper surface 26 of the support 6 forming part of the tibial component 3. The leaf 21 comprises an eyelet 38 which defines a bore or hole 30 for and surrounds the pin 35. In order to assemble the second tibial component 3 with the femoral component 1, the third leaf 21 is inserted into the housing including the walls 61, 65 of the second leaf, the pin 35 is inserted through a bore or hole 40 of the wall 65 (FIG. 4), thereupon through the bore 30 of the leaf 21 and ultimately into a blind bore or hole 39 of the wall 61. The next step involves introduction of the bearing 23 (on the shaft 22) into the bore or hole 24 of the third leaf 21.

The first leaf 5 is located in a plane which is normal to the upper side or surface 26 of the support 6 forming part of the first tibial component 2. The plane 11 halves the leaf 5 (see FIG. 6), i.e., the leaf 5 comprises two mirror symmetrical halves 41. The thickness 42 of the leaf 5 matches or closely approximates the distance between the walls 61, 65 of the second leaf, and the thickness 43 (FIG. 8) of the third leaf 21. Thus, the chamber 46 which is flanked by the internal surfaces 44 and 45 of the walls 61, 65 can snugly receive the leaf 5 or the leaf 21. Thus, the only movement the leaf 5 or 21 in the chamber 46 can perform relative to the housing of the femoral component 1 is that about the axis 31 of the pintle 35.

Figure 7:
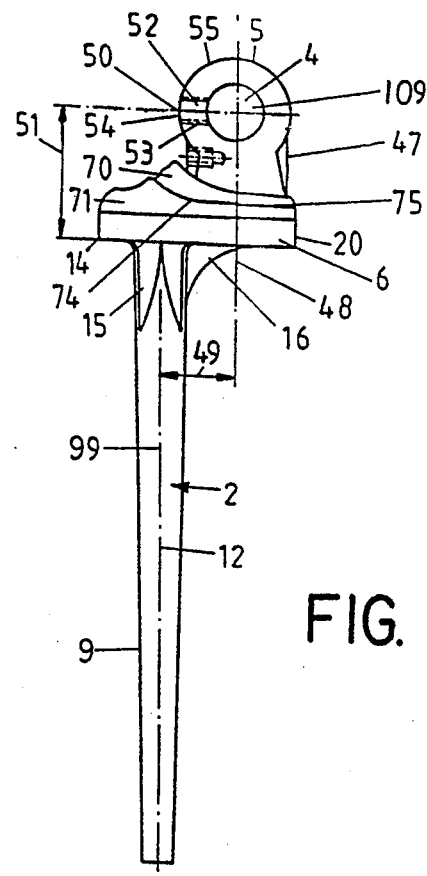
FIG. 7 is a view of the first tibial component as seen from the left-hand side of FIG. 6.

The leaf 5 of the first tibial component 2 is nearer to the rear end 20 than to the front end 14 of the respective support 6 (see particularly FIG. 7). Thus, the rear edge face 47 of the leaf 5 is or can be at least substantially flush with the rear end face (at the rear end 20) of the respective support 6. The distance 49 (FIG. 7) of the plane 48 of the axis 31 of a properly inserted pintle 35 from the axis 12 of the shank 9 of the first tibial component 2 is the same as the distance between the planes 99 and 48 of the axes 12 and 31 in FIG. 9. The plane 99 is normal to the plane 11 and includes the axis 12 of the shank 9 of the tibial component 2 or 3. The through bore or hole 109 in the leaf 5 receives the central portion of a properly inserted pintle 35 when the latter articulately connects the leaf 5 to the leaf including the walls 61, 65 forming part of the housing of the femoral component 1. The axis of the bore 109 is normal to the plane 11. The aforementioned distance 51 (FIG. 7) between the plane of the axis 31 and the upper side 26 of the support 6 of the tibial component 2 is the same as the distance between the axis 31 and the upper side of the support 6 forming part of the tibial component 3.

The properly inserted pintle 35 can be releasably secured to the housing of the femoral component 1 by a grub screw 52 (FIGS. 1, 2 and 7) having external threads movable into mesh with internal threads 53 of a tapped radial bore 54 provided in the external surface of the eyelet 55 of the leaf 5. Once the grub screw 52 is driven home, the pintle 35 is held against rotation relative to the leaf 5 but its end portions 34 are free to turn in the through bore 40 of the wall 65 and in the blind bore 39 of the wall 61, i.e., the pintle can turn relative to the leaf including the walls 61, 65 but cannot turn relative to the leaf 5.

The housing of the femoral component 1 is designed in such a way that it can receive the leaf 5 of the first tibial component 2 or the leaf 21 of the second tibial component 3 without any changes of the femoral component. This enhances the versatility of the novel kit and reduces the cost of the prosthesis which is assembled by the surgeon in charge of implanting a flexion-type or a rotational knee joint prosthesis. Though it is possible to provide the novel kit with two pintles, namely (a) a pintle which does not have a socket 28, and (b) a pintle which is provided with such socket, the provision of two different pintles is not necessary because a pintle having the socket 28 can be used with equal advantage to secure the leaf 5 to the leaf including the walls 61 and 65.

Figure 4:
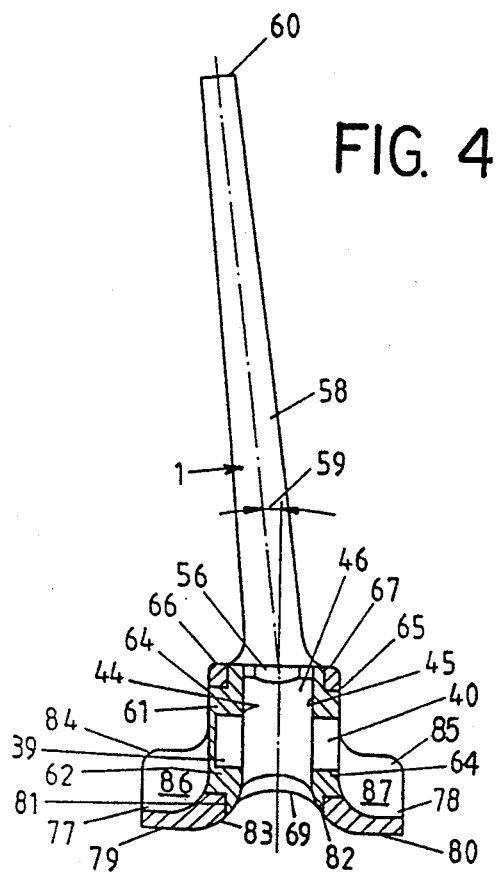
FIG. 4 is a smaller-scale sectional view of the femoral component, substantially as seen in the direction of arrows from the line IV—IV in FIG. 3.

The housing of the femoral component 1 further comprises a top wall 56 which overlies the chamber 46 and is spaced apart from the open underside of the housing. The front or patellar edge face 57 of the top wall 56 is flush with or is at least close to the front side of the adjacent lower end of the shank 58 forming part of the femoral component 1. The valgus angle (namely the angle between the axis of the shank 58 and a plane (11) which is normal to the axis 31 of the pintle 35 in the bores 39, 40 of the second leaf including the walls 61 and 65) is shown in FIG. 4, as at 59. This angle can be in the range of 3° to 8° and corresponds to the valgus position of the femur.

The shank 58 tapers gradually in a direction from the too wall 56 toward its free upper end 60. For example, the shank can constitute an elongated slender cone whose larger-diameter end is integral with the top wall 56 (shank 58) or with the respective support 6 (shank 9 of the tibial component 2 or 3). It is presently preferred to provide each of the components 1 to 3 with a shank 9, 9 or 58 which has a conical external surface with one or more longitudinally extending facets or flats (not specifically shown in the drawing). However, it is equally possible to provide the component 1, 2 or 3 with a shank 58, 9 or 9 which has a polygonal (e.g., rectangular) cross-sectional outline with the longer sides of the rectangle extending in substantial parallelism with the axis 31. The corners of a shank having a polygonal cross-sectional outline are preferably rounded, and its lower end expands and merges gradually into the upper side of the top wall 56 or into the underside 10 of the respective support 6.

The walls 61, 65 of the second leaf are disposed in parallel planes which are normal to the axis 31 of the pintle 35. In the embodiment which is shown in FIG. 4, the internal surfaces 44 and 45 of the walls 61 and 65 are parallel to the external surfaces 64, 63. The upper edge portions 66, 67 of the walls 61, 65 merge into the adjacent portions of the top wall 56 to form therewith a substantially block-shaped structure surrounding three sides of the chamber 46 for the leaf 5 or 21. A front surface 68 of the housing including the walls 61, 65 and 56 is flush or practically flush with the front edge face 57 of the shank 58. The lowermost portion of the front surface 68 is adjacent a follower 69 forming part of the housing of the femoral component 1 and being bounded by a concave surface which engages the complementary surface of a cam 70 on the support 6 of that tibial component 2 or 3 whose leaf 5 or 21 is articulately connected to the leaf including the walls 61 and 65 when the components 1 and 2 or 1 and 3 are maintained in the extended positions of FIG. 11. The cam 70 is provided on an upwardly extending track member 71 on the respective support 6 (see particularly FIGS. 6 and 7). The track member 71 abuts the upper side or surface 26 of the support 6. One or more screws 72 (FIG. 10) and/or other suitable fasteners may be provided to fixedly secure the track member 71 to the respective support 6. The cam 70 serves to properly guide and properly orient the femoral component 1 relative to the tibial component 2 or 3 (and/or vice versa) at least during pivoting of the components 1 and 2 or 1 and 3 relative to each other between the first and second positions which are respectively shown in FIGS. 11 and 12.

Figure 12:
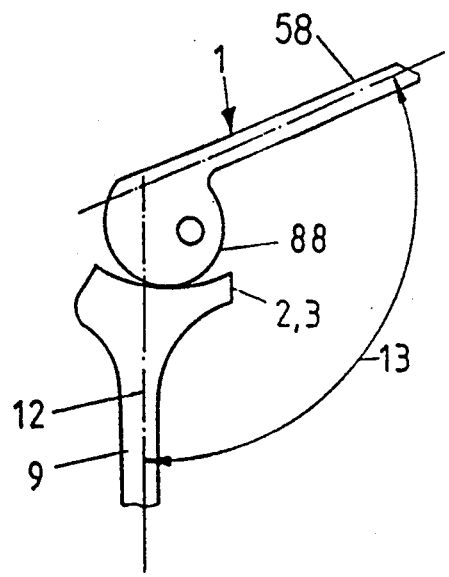
FIG. 12 is a similar schematic smaller-scale elevational view showing the femoral component and one of the tibial components in second positions relative to each other in which the shanks of such components make an oblique angle.

The track member 71 has two top faces 73 and 74 which are disposed at opposite sides of the respective leaf 5 or 21 and slope downwardly and outwardly toward the lateral portions 18 and 19 of the respective support 6, i.e., away from the respective leaf 5 or 21. Portions 75 and 76 of the top faces 73, 74 are adjacent complementary surfaces 79, 80 which are provided on two skids 77, 78 forming part of the walls 61 and 65, respectively. More particularly, the skids 77 and 78 are respectively provided on wing-shaped lateral extensions 86 and 87 of the respective walls 61 and 65. The purpose of the wing-shaped extensions 86, 87 and of their skids 77, 78 is to take up lateral stresses during pivoting of the components 1 and 2 or 1 and 3 relative to each other as well as in the end positions which are shown in FIGS. 11 and 12. This relieves the pintle 35 as well as the leaves 61, 65 and 5 or 61, 65 and 21, depending upon whether the assembled prosthesis is a flexion-type or a rotational prosthesis. The areas of the surfaces 79, 80 of the skids 77, 78 are large to reduce the stresses per unit area when the corresponding portions 75, 76 of the top faces 73, 74 of the adjacent track member 71 are called upon to take up stresses which are being transmitted by the femoral component 1. The wing-shaped extensions 86, 87 extend laterally from the lower ends 81, 82 of the parallel portions of the respective walls 61, 65. The surface 79, 80 of each of the two skids 77, 78 has a pronounced convex portion 83 which is adjacent the inlet at the lower end of the chamber 46. The extensions 86, 87 are respectively provided with reinforcing portions 84 and 85 (FIG. 4). The upper sides of the skids 77 and 78 serve as abutments for the lower end of the femur when the implanting of the shank 58 is completed.

Figure 3:
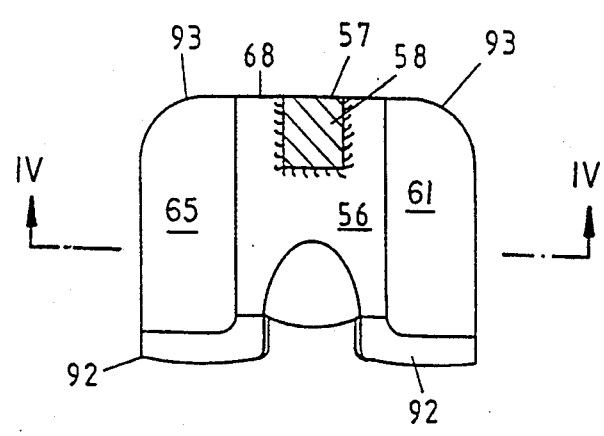
FIG. 3 is a partial too plan view and partial horizontal sectional view, substantially as seen in the direction of arrows from the line III—III in FIG. 2.
Figure 5:
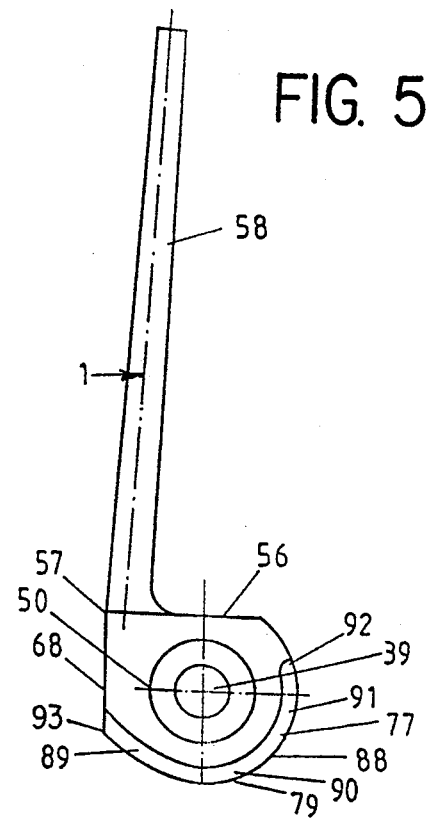
FIG. 5 is an elevational view of the femoral component as seen from the left-hand side of FIG. 4.
Figure 6:
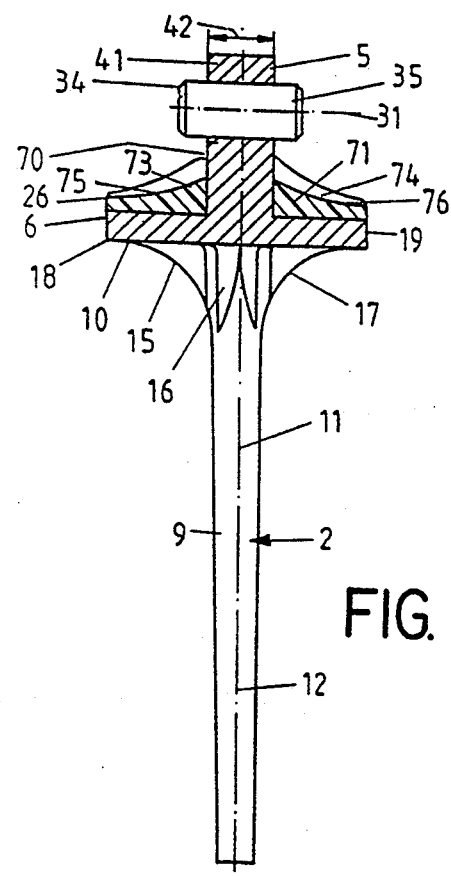
FIG. 6 is a partly elevational and partly vertical sectional view of the first tibial component as seen in the direction of arrows from the line IV—IV in FIG. 3.

The undersides of the skids 77 and 78 are bounded in part by convex surfaces 88 (see particularly FIG. 5). Each of these convex surfaces can extend along an arc of approximately 180°, i.e. substantially halfway around a pintle 35 which connects the leaf including the walls 61, 65 with the leaf 5 or 21. The radii of curvature of front portions 89 of the convex surfaces 88 are larger than the radii of curvature of the rear portions 91 of such surfaces. The configuration of the convex surfaces 88 can be such that their radii of curvature decrease gradually from the front surface 68 of the housing including the walls 61, 65 and 56 toward the rear end of the housing. In the embodiment of FIG. 5, the curvature of the front portions 89 of the convex surfaces 88 is more or less constant from the front surface 68 to the plane 48 of FIG. 5, and the curvature of the next or median portions 90 of such convex surfaces is more pronounced. The curvature of the rear portions 91 of the surfaces 88 is even more pronounced (i.e., their radii of curvature are even smaller). The front ends 93 (FIGS. 3 and 5) of the surfaces 88 are located at a level a few degrees below the horizontal plane 50 extending through the axis 31 of a pintle 35 in the bores 39, 40 of the leaf including the walls 61 and 65. On the other hand, the rearmost ends 92 of the convex surfaces 88 are located at a level above the plane 50, preferably by the same number of degrees as that between this plane and the front ends 93 of the convex surfaces 88.

The plane 99 (FIG. 7) which is normal to the plane 11 and includes the axis 12 of a shank 9 is offset from the front end 14 of the respective support 6 in a direction toward the rear end 20. The arrangement is preferably such that the distance of the plane 99 from the front end 14 is approximately one-third the distance of the front end 14 from the rear end 20. Thus, the shank 9 is nearer to the front end than to the rear end of the respective support 6, in contrast to the leaf 5 or 21 which is nearer to the rear end 20.

As mentioned above, the distance 51 of the horizontal plane 50 of the axis 31 from the upper side 26 of a support 6 can be in the range of 25 to 30 min. The diameter of the pintle 35 need not exceed 20 mm, and the distance of the convex surfaces 88 from the axis 31 of the pintle 35 can be in the range of 20 to 25 min. The distance of the front surface 68 of the housing of the femoral component 1 from the front end 14 of the support 6 which happens to be articulately connected to the leaf including the walls 61 and 65 is preferably in the range of 10 to 15 mm (this holds true when the components 1 and 2 or 1 and 3 are maintained in the extended positions of FIG. 11). At such time, the skids 77, 78 of the walls 61, 65 extend rearwardly beyond the rear end 20 of the support 6 by a distance of 10 to 15 min.

The front surface 68 is not or need not be parallel to the aforementioned plane 99 when the components 1 and 2 or 1 and 3 assume the extended positions of FIG. 11. At such time, the surface 68 makes with the upper side 26 of the respective support 6 a relatively large acute angle. The lowermost portion 69 (FIG. 11) of the surface 68 is then located at the level of portions 75, 76 of the top faces 73, 74 of the track member 71 and is substantially flush with the foremost part of the upper end of the respective shank 9 at the underside 10 of the corresponding support 6.

The axis of the femoral shank 58 is located in a plane which is parallel to the plane 99 when the components 1 and 2 or 1 and 3 assume the extended positions of FIG. 11. This axis is offset relative to the axis of the shank 9 of the component 2 or 3 by a distance of 0.5 to 4 mm (in a direction away from the axis 31 of the pintle 35.

The rear portion 20 of each support 6 has a substantially centrally located recess 94 (FIG. 10) which is adjacent the rear edge face 47 of the respective leaf 5 or 21 and extends toward the respective front end 14 and is flanked by outwardly bulging convex portions 95, 96 of the support. The portions 95 and 96 are provided with the aforementioned portions 75, 76 of top faces 73, 74 which can be contacted by the skids 77 and 78, respectively. The surface portions 75 and 76 constitute parts of a substantially horseshoe-shaped surface and are connected to each other, in the region of the front end 14 of the respective support 6, by a surface which is provided on a part 97 constituting or including the track member 71.

As already mentioned above, the distance of the upper side 26 of a support 6 from the plane 50 of the axis 31 of the properly inserted pintle 35 is preferably between 25 and 30 mm. The distance between the external surfaces 64 of the walls 61, 65 forming part of the housing of the femoral component 1 can be in the range of 30 to 35 mm, preferably close to 30 mm. The thickness of each of the walls 61, 65 can be between 5 and 8 mm, preferably close to 5 mm.

The free outer ends of the shanks 58 and 9 can be provided with centering portions 98 which facilitate predictable introduction of such shanks into the holes provided therefor in a femur (shank 58) or in a tibia (shank 9). Each of the prongs 58 can have a substantially star-shaped cross-sectional outline.

An important advantage of the improved knee joint prosthesis kit is that its versatility exceeds that of heretofore known knee joint endoprostheses. Thus, the dimensions of the housing of the femoral component 1 are selected in such a way that this housing can snugly receive the leaf 5 of the tibial component 2 for mere pivotal movement abut the axis 31 of the pintle 35, or the leaf 21 of the tibial component 3 for pivotal movement about the axis 31 and/or rotational movement about the axis 8. As already mentioned above, the surgeon in charge Of implanting a flexion-type or combined flexion- and rotation-type knee joint endoprosthesis can reach a last-minute decision as to which of the two types of knee joint prostheses is more satisfactory for implantation into a knee of a particular patient, and such decision can be reached while the operation is already in progress. Thus, the surgeon in charge can take into consideration each and every factor, including those which can be ascertained prior to start of surgery as well as those which become apparent only while the surgery is already in progress. The mode of implantation is the same or practically the same, i.e., the implantation of the shank 58 of the femoral component 1 can be followed or preceded by implantation of the shank 9 of the tibial component 2 or 3. This is due to the fact that those parts of the tibial components 2 and 3 which are to be implanted into a tibia are the same. Thus, surgical exposure of portions of the femur and tibia and the preparation of the exposed condyles of such bones for implantation of the shanks 58 and 9 can proceed in the same way irrespective of whether the tibia is to receive the shank 9 of the component 2 or the shank 9 of the component 3. The decision to implant the tibial component 2 or 3 can be reached within the framework of a tentative pre-positioning, i.e., a preliminary insertion of the prosthesis without cement. This enables the surgeon to take into consideration each and every parameter which should be considered in connection with the selection of an optimal prosthesis.

In accordance with the presently prevailing practice, attempts to take into consideration all factors which are important in connection with the selection of an appropriate knee joint endoprosthesis involved the utilization of prostheses which were not identifiable (unequivocally) as belonging to a first type or to a different second type. For example, experiments were carried out with prostheses which were basically of the flexion type but were designed to establish a certain amount of play. A drawback of such prostheses is that they are incapable of accurately determining the exact nature of pivoting of the femoral and tibial components relative to each other and/or that they are incapable of permitting adequate rotational movements of the tibial and femoral components relative to one another. Moreover, the wear upon relatively movable parts of prostheses wherein the femoral and tibial components are articulately connected to each other with a certain amount of play is very pronounced which is unacceptable for obvious reasons. Still further, since the nature of movements which can be performed by such components relative to each other is not sufficiently predictable, the patient is often uncomfortable and cannot utilize the mended knee with the same degree of assurance as a patient whose knee contains a standard flexion-type or a standard rotational prosthesis.

A surgeon who has access to the improved kit can decide to utilize a plain flexion-type endoprosthesis or a rotation-type endoprosthesis upon final determination (after preliminary implantation without cement) as to which of the two types of prostheses is best suited for a particular patient. Thus, once implanted, the improved prosthesis enables the patient to utilize her or his knee in the best possible manner, depending on the nature of affliction and/or deformity (such as genu varum, genu valgum, genu flexure or genu laxum) which necessitated the implantation of a knee joint prosthesis. Moreover, the possibility to immediately select an optimal prosthesis ensures that the patient need not be subjected to a secondary operation involving the implantation of a different prosthesis, resection and other treatments which could involve highly undesirable, costly and traumatic bone losses.

Heretofore, experts in the field of developing knee joint prostheses were of the opinion that the design of a satisfactory flexion-type prosthesis must depart from the design of a satisfactory rotation-type prosthesis. It has been determined that such reservations are not warranted because a large majority of constituents which form part of the improved kit can be assembled into a flexion-type prosthesis or into a rotation-type prosthesis by the simple expedient of selecting the tibial component 2 or the tibial component 3. The reason is that the dimensions of the housing of the femoral component 1 are selected in such a way that this housing can cooperate with the leaf 5 of the tibial component 2 and with the pintle 35 to constitute a flexion-type prosthesis, or with the tibial component 3 and with the pintle 35 to constitute a rotational prosthesis. The stability of either of the two prostheses is highly satisfactory because it is not necessary to resort to an overdimensioning or underdimensioning of the component 1, 2 and/or 3 in order to ensure long useful life of the prosthesis, be it a relatively simple flexion-type prosthesis (including the parts 1, 2 and 35) or a more versatile rotation prosthesis (including the parts 1, 3 and 35).

The feature that the axis 12 of the tibial component 2 or 3 is normal to the underside 10 of the respective support 6 in the plane 11 as well as in the plane 99 which is normal to the plane 11 is desirable and advantageous because this ensures highly satisfactory transmission of forces from the support 6 to the respective shank 9 and thence into the tibia.

The skids 76 and 77 exhibit the advantage that they can transmit forces from the femur and femoral component 1 to the support 6 of the tibial component 2 or 3 at both sides of a plane (such as the plane 11) which is normal to the axis 31 of the properly installed pintle 35. This holds true irrespective of whether the femoral component 1 is coupled with the tibial component 2 or with the tibial component 3.

An important advantage of the concave follower 69 and of the associated cam 70 is that these parts can relieve the pintle 35 of stresses which tend to tilt the pintle relative to the walls 61, 65 of the housing of the femoral component 1 and/or relative to the leaf 5 or the leaf 21. Such stabilizing action is particularly important (and has been found to be highly reliable) when the femoral component 1 and the tibial components 2 or 3 are caused to assume the extended positions which are shown in FIG. 11. The follower 69 and the cam 70 further serve to oppose the tendency of the support 6 of the tibial component 2 to turn relative to the housing of the femoral component 1, i.e., the pintle 35 of a prosthesis which includes the components 1 and 2 need not be called upon to take up and counteract the just discussed stresses.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. A knee joint prosthesis kit comprising first and second tibial components each including an elongated shank configured to be implanted in a tibia; a femoral component having a shank implantable in a femur; and means for joining said femoral component to a selected one of said tibial components including means for movably connecting said first tibial component with said femoral component so that the first tibial component is pivotable relative to the femoral component only about a first axis, and means for movably securing said second tibial component to said femoral component so that the second tibial component is pivotable relative to said femoral component about said first axis as well as about a second axis which is at least substantially normal to said first axis, said first axis being nearer to a dorsal end than to a patellar end of said connecting means.

2. The kit of claim 1, wherein said connecting means comprises a first hinge having a first leaf provided on said first tibial component, a second leaf provided on said femoral component, and a pintle arranged to movably connect said leaves to each other to define said first axis between said femoral and tibial components while said leaves are connected to each other.

3. The kit of claim 2, wherein said second tibial component comprises a support at one end of the shank of said second tibial component and said means for securing said second tibial component to said femoral component comprises a second hinge having a third leaf, said pintle and said means for movably mounting said third leaf on said support for rotation about said second axis, said pintle being arranged to movably connect said second and third leaves to each other and to define said first axis while said second and third leaves are connected to each other.

4. The kit of claim 3, wherein said first tibial component further comprises a second support disposed at one end of the shank of said first tibial component and carrying said first leaf, said second support having a side facing away from the first leaf and the shank of said first tibial component being substantially normal to said side of said second support.

5. The kit of claim 4, wherein the shank of each of said tibial components is pivotable in a plane which is normal to said first axis when the leaf of either of said tibial components is connected to said second leaf.

6. The kit of claim 3, wherein said first tibial component further comprises a second support disposed at one end of the shank of the first tibial component and carrying said first leaf, said second support having a side facing away from the first leaf and said second support having a patellar end and a dorsal end, the shank of said first tibial component extending from said side and at least said first tibial component having a plurality of reinforcing portions disposed at said side and extending between said second support and the adjacent end of the shank of said first tibial component.

7. The kit of claim 6, wherein said reinforcing portions include a rib disposed at the dorsal end of said second support in a first plane which is normal to said first axis when the leaf of said first tibial component is connected to said second leaf, said reinforcing portions further including two ribs disposed in a second plane which is substantially normal to said first plane.

8. The kit of claim 3, wherein said femoral component comprises a housing disposed at one end of the respective shank and including said second leaf, said first leaf being at least partially confined in said housing when said first and second leaves are connected to each other and said third leaf being at least partially confined in said housing when said second and third leaves are connected to each other.

9. The kit of claim 8, wherein said housing comprises two spaced-apart walls constituting said second leaf, said walls having skids which are adjacent said support when said third leaf is connected to said second leaf, said first tibial component further comprising a support disposed at one end of the respective shank and carrying said first leaf, said skids being adjacent said support of said first tibial component when said first leaf is connected to said second leaf.

10. The kit of claim 9, wherein each of said supports comprises a track for said skids.

11. The kit of claim 10, wherein said walls are disposed at opposite sides of a plane which is normal to said first axis when said second leaf is connected to one of said first and third leaves, each of said tracks having two portions, one for each of said skids, and each of said supports having two lateral portions which are disposed at opposite sides of said plane when the leaf of the respective tibial component is connected to said second leaf, each lateral portion of each support carrying one portion of the respective track.

12. The kit of claim 11, wherein each of said supports further comprises a patellar end and said lateral portions of each support comprise top faces sloping upwardly toward a cam at the patellar end of the respective support.

13. The kit of claim 12, wherein said femoral component and the tibial component whose leaf is connected to said second leaf are pivotable relative to each other between extended first and mutually inclined second positions, said femoral component having a follower which abuts one of said cams when said femoral component and the tibial component including said one cam assume said first positions relative to each other.

14. The kit of claim 3, wherein said first tibial component further includes a support disposed at one end of the respective shank, each of said supports having a patellar end and a dorsal end spaced apart from the respective patellar ends said ends of said shanks of said tibial components being spaced apart from the patellar ends of the respective supports.

15. The kit of claim 14, wherein each of said tibial components further comprises reinforcing portions disposed in a plane which is substantially parallel to said first axis when the leaf of the respective tibial component is connected to said second leaf, said reinforcing portions being disposed between the supports and said ends of the respective shanks and each of said planes being nearer to the patellar end than the dorsal end of the respective support.

16. The kit of claim 14, wherein each of said tibial components further comprises a reinforcing rib disposed between the respective support and said end of the respective shank and extending at least close to the dorsal end of the respective support.

17. The kit of claim 3, wherein said first tibial component further includes a support disposed at one end of the respective shank and carrying the respective leaf, each of said supports having a patellar end and a dorsal end and said first axis being nearer to the dorsal end than to the patellar end of the support carrying the leaf which is connected with said second leaf.

18. The kit of claim 3, wherein said first tibial component further includes a support disposed at one end of the respective shank and carrying the respective leaf, said first axis being spaced apart from either of said supports a distance of 25–30 mm when the leaf of the respective tibial component is connected to said second leaf.

19. The kit of claim 18, wherein said pintle has a diameter at least approximating 20 mm.

20. The kit of claim 3, wherein said first tibial component further includes a support disposed at one end of the respective shank, said femoral component further comprising a housing having two spaced apart walls together forming said second leaf and having skids confronting either of said supports when the leaf of the respective tibial component is connected to said second leaf, said skids having convex surfaces confronting the support of the tibial component whose leaf is connected to said second leaf and said convex surfaces being spaced apart from said first axis a distance of 20–25 mm.

21. The kit of claim 20, wherein said convex surfaces extend along arcs of approximately 180 degrees.

22. The kit of claim 20, wherein said housing has a patellar end and a dorsal end and includes a front surface disposed at said patellar end thereof and extending to the respective shank, said convex surfaces including front portions having first radii of curvature and being adjacent said front surface of said housing and rear portions having smaller second radii of curvature and being adjacent said dorsal end of said housing.

23. The kit of claim 20, wherein said housing has a patellar end and a dorsal end and a front surface at said patellar end thereof, said convex surfaces having front portions at said front surface.

24. The kit of claim 23, wherein each of said supports includes a patellar end and a dorsal end, said femoral component and the tibial component whose leaf is connected to said second leaf being pivotable relative to each other about said first axis between extended first positions and mutually inclined second positions, said front surface of said housing being offset from the patellar end toward the dorsal end of the support forming part of that tibial component whose leaf is connected to said second leaf.

25. The kit of claim 24, wherein said housing further comprises a concave follower confronting the support of that tibial component whose leaf is articulately connected to said second leaf, each of said supports including a cam which is adjacent said follower in the first positions of said femoral component and the respective tibial component.

26. The kit of claim 3, wherein said first tibial component further comprises a support disposed at one end of the respective shank and carrying said first leaf, each of said supports having a patellar end and a dorsal end and said femoral component further comprising a housing having two spaced-apart walls which constitute said second leaf, said housing further having skids confronting the support of that tibial component whose leaf is connected to said second leaf, said femoral component and the tibial component whose leaf is connected to said second leaf being pivotable relative to each other abut said first axis between extended first positions and mutually inclined second positions and said housing further having a dorsal end extending beyond the dorsal end of either of said supports when the leaf of the respective tibial component is connected to said second leaf and said femoral component and the respective tibial component assume said first positions.

27. The kit of claim 26, wherein said housing has a patellar end and a front surface at said patellar end thereof, said supports having upper sides and the upper side of the support carrying the leaf which is connected with said second leaf making an acute angle with said front surface in the extended positions of said femoral component and the tibial component whose leaf is connected to said second leaf.

28. The kit of claim 27, wherein said front surface has a portion which is adjacent said skids, said ends of said shanks of said tibial components having front portions each of which is at least substantially aligned with said portion of said front surface when the leaf of the respective tibial component is connected to said second leaf and the femoral component and the tibial component whose leaf is connected to said second leaf assume said first positions.

29. The kit of claim 3, wherein said femoral component further comprises a housing having two spaced-apart walls constituting said second leaf, a patellar end, a dorsal end, a front surface at said patellar end thereof and a top wall which is substantially normal to said front surface and carries the shank of said femoral component.

30. The kit of claim 29, wherein the shank of said femoral component has an end which is adjacent said front surface.

31. The kit of claim 3, wherein each of said shanks has a longitudinal axis, said femoral component and the tibial component whose leaf is connected to said second leaf being pivotable relative to each other abut said first axis to and from extended positions in which the axis of the shank of said femoral component is parallel to the axis of the shank of that tibial component whose leaf is connected to said second leaf.

32. The kit of claim 31, wherein the axis of the shank of that tibial component whose leaf is connected to said second leaf is nearer to said first axis than the axis of the shank of said femoral component when said femoral component and the tibial component whose leaf is connected to said second leaf assume said extended positions.

33. The kit of claim 32, wherein the axis of the shank of said femoral component and the axis of the shank forming part of that tibial component whose leaf is connected to said second leaf are disposed in substantially parallel planes spaced apart from each other a distance of 0.5 to 4 mm in the extended positions of said femoral component and the tibial component whose leaf is connected to said second leaf.

34. The kit of claim 3, wherein said femoral component and the tibial component whose leaf is connected to said second leaf are pivotable relative to each other to and from extended positions in a plane which is normal to said first axis, said shank of said femoral component having an axis which makes with said plane an acute valgus angle in the extended positions of said femoral component and the tibial component whose leaf is connected to said second leaf.

35. The kit of claim 34, wherein said acute angle is between 3° and 8°.

36. The kit of claim 3, wherein at least one of said shanks tapers in a direction away from the respective leaf.

37. The kit of claim 36, wherein said at least one shank resembles an elongated slender cone.

38. The kit of claim 36, wherein said at least one shank has a substantially smooth external surface.

39. The kit of claim 36, wherein said at least one shank has a substantially circular cross-sectional outline.

40. The kit of claim 3, wherein at least one of said shanks has a facetted external surface.

41. The kit of claim 3, wherein said femoral component further comprises a housing including two-spaced apart walls which constitute said second leaf, said housing having a front surface and said walls having external surfaces which are at least substantially normal to said front surface.

42. The kit of claim 41, wherein said external surfaces are plane surfaces and said walls have aligned bores for portions of said pintle.

43. The kit of claim 3, wherein each of said shanks has an end which is remote from the respective leaf and at least one of said remote ends is provided with centering means.

44. The kit of claim 3, wherein said femoral component comprises a housing having two spaced-apart walls constituting said second leaf and having external surfaces spaced apart from each other a distance of 30 to 35 min.

45. The kit of claim 44, wherein said distance at least approximates 30 min.

46. The kit of claim 3, wherein said femoral component comprises a housing having two spaced-apart walls constituting said second leaf, each of said walls having a thickness of 5 to 8 mm.

47. The kit of claim 46, wherein said thickness at least approximates 5 min.

48. The kit of claim 3, wherein said first tibial component further comprises a support disposed at one end of the respective shank and carrying said first leaf, said femoral component comprising a housing having two spaced-apart walls which constitute said second leaf, said walls comprising extensions having sides which are engaged by a portion of a femur into which the shank of said femoral component is implanted.

49. The kit of claim 48, wherein each of said walls has an external surface which is adjacent the respective side and each of said extensions further comprises a skid having a surface located opposite the side of the respective extension and confronting the support of that tibial component whose leaf is connected to said second leaf.

50. The kit of claim 49, wherein said sides and the surfaces of the respective skids have substantially identical length as seen from a front side toward a rear side of said housing.

51. The kit of claim 49, wherein each of said sides merges gradually into the external surface of the respective wall.

52. The kit of claim 49, wherein each of said skids has a thickness of 1 to 3 min.

53. The kit of claim 49, wherein each of said supports includes a patellar end and a dorsal end and the dorsal end of each of said supports is provided with a recess and two convex portions flanking the respective recess, said convex portions of the support carrying the leaf which is connected to said second leaf.

54. The kit of claim 53, wherein said convex portions have surfaces extending to said patellar ends of said support and each of said supports further comprises a cam having a surface extending between the surfaces of the respective convex portions.

55. The kit of claim 53, wherein said first leaf has an edge face adjacent the dorsal end of the respective support and adjacent the respective recess.

56. The kit of claim 55, wherein the support of said first tibial component has a surface facing away from the respective shank and disposed at a distance of 25 to 30 mm from said first axis when said first leaf is connected with said second leaf.

57. The kit of claim 49, wherein said surfaces of said skids are elongated and include convex portions extending longitudinally thereof.

58. The kit of claim 3, wherein said means for movably mounting said third leaf on said support includes a shaft provided on said support and a bearing surrounding said shaft and received in a hole of said third leaf.

59. The kit of claim 58, wherein said bearing is spaced apart from said support and includes a portion extending into a socket of said pintle when said third leaf is connected to said second leaf.

* * * * *